US008638236B2

(12) United States Patent
Chen et al.

(10) Patent No.: US 8,638,236 B2
(45) Date of Patent: Jan. 28, 2014

(54) METHODS AND APPARATUS FOR APPLYING TACTILE PRESSURE SENSORS

(75) Inventors: An M. Chen, San Diego, CA (US); Jack Steenstra, San Diego, CA (US)

(73) Assignee: QUALCOMM Incorporated, San Diego, CA (US)

(*) Notice: Subject to any disclaimer, the term of this patent is extended or adjusted under 35 U.S.C. 154(b) by 717 days.

(21) Appl. No.: 12/712,873

(22) Filed: Feb. 25, 2010

(65) Prior Publication Data

US 2011/0205081 A1 Aug. 25, 2011

(51) Int. Cl.
*G08C 19/16* (2006.01)
*G01S 19/19* (2010.01)

(52) U.S. Cl.
USPC ............. 340/870.01; 340/870.03; 342/357.57

(58) Field of Classification Search
USPC ........... 340/870.01, 870.18, 870.19; 702/150; 455/575.1, 566; 345/157, 173; 342/357.57
See application file for complete search history.

(56) References Cited

U.S. PATENT DOCUMENTS

| 5,376,497 | A  | * | 12/1994 | Kawata et al. | 430/191 |
| 5,617,117 | A  | * | 4/1997 | Kataoka et al. | 345/157 |
| 7,406,400 | B2 | * | 7/2008 | Yano et al. | 702/184 |
| 7,468,927 | B1 |   | 12/2008 | Battista |  |
| 7,529,639 | B2 | * | 5/2009 | Rasanen et al. | 702/150 |
| 7,973,274 | B2 | * | 7/2011 | Kuniyoshi et al. | 250/231.19 |
| 8,095,180 | B2 | * | 1/2012 | Lee et al. | 455/556.1 |
| 8,116,831 | B2 | * | 2/2012 | Meitzler et al. | 455/575.1 |
| 2007/0298896 | A1 |   | 12/2007 | Nusbaum et al. |  |
| 2009/0153289 | A1 | * | 6/2009 | Hope et al. | 340/5.1 |
| 2009/0225046 | A1 | * | 9/2009 | Kim et al. | 345/173 |
| 2009/0240118 | A1 |   | 9/2009 | Aggarwal |  |
| 2010/0328051 | A1 | * | 12/2010 | Hale et al. | 340/407.1 |
| 2011/0205081 | A1 | * | 8/2011 | Chen et al. | 340/870.01 |

FOREIGN PATENT DOCUMENTS

| DE | 202006019191 U1 | 5/2008 |
| EP | 1702769 A2 | 9/2006 |
| JP | H0889482 A | 4/1996 |
| JP | 2005510694 A | 4/2005 |
| JP | 2005144106 A | 6/2005 |
| JP | 2005517935 A | 6/2005 |
| JP | 2005326375 A | 11/2005 |
| JP | 2008513745 A | 5/2008 |
| JP | 2009031865 A | 2/2009 |

OTHER PUBLICATIONS

Benbasat A Y et al., "A wireless modular sensor architecture and its application in shoe gait analysis", Proceedings of IEEE Sensors 2003 (IEEE Cat. N0.03CH37498) IEEE Piscataway, NJ, USA; [IEEE International Conference on Sensors], vol. Conf 2, Oct. 22, 2003, pp. 1086-1091, vol. 2, XP010690943, DOI: DOI:10.1109/ICSENS. 2003.1279111 ISBN: 978-0-7803-8133-9.
International Search Report and Written Opinion—PCT/US2011/ 026342—ISA/EPO—Aug. 5, 2011.

* cited by examiner

*Primary Examiner* — Peguy Jean Pierre
(74) *Attorney, Agent, or Firm* — Charles Chesney

(57) ABSTRACT

A method of wireless communication includes transmitting configuration information to a tactile pressure sensor apparatus, receiving pressure sensor data from the tactile pressure sensor apparatus based on the configuration information, and providing the received tactile pressure sensor data to a user.

61 Claims, 12 Drawing Sheets

| Byte | Description |
|---|---|
| 0 | Transmit Rate (units of 0.1 Hz) |
| 1 | Sample Rate (units of 0.5 Hz) |
| 2 | Sensor 0 Size |
| 3 | Sensor 1 Size |
| 4 | Sensor 2 Size |
| 5 | Sensor 3 Size |
| 6 | Sensor 4 Size |
| 7 | Sensor 5 Size |
| 8 | Sensor 6 Size |
| 9 | Sensor 7 Size |

| Byte | Description | Notes |
|---|---|---|
| 0 | Header Byte | Each header byte is 0xF, which cannot naturally appear in data, so it can be used to identify the start. |
| 1 | Header Byte | |
| 2 | Version | 0x00 for now: for future expansion |
| 3 | Device Type | Used for future expansion |
| 4 | Device ID | |
| 5 | Frame Counter | Used to detect dropped frames |
| 6 | System Status | |
| 7 | Timestamp 0 | 4-byte Timestamp of data (1 ms base) |
| 8 | Timestamp 1 | |
| 9 | Timestamp 2 | |
| 10 | Timestamp 3 | |
| 11 | Data Byte 0 | Data from each sensor, including slave devices, one complete frame at a time, (i.e. all data from Sensor 0, all data from Sensor 1, etc.) If connection to slave is lost, zeros are returned for its data |
| 12 | Data Byte 1 | |
| ... | ... | |
| 11 + (N-1) | Data Byte N-1 | |
| 11 + N | Checksum | Error checking |

FIG. 9

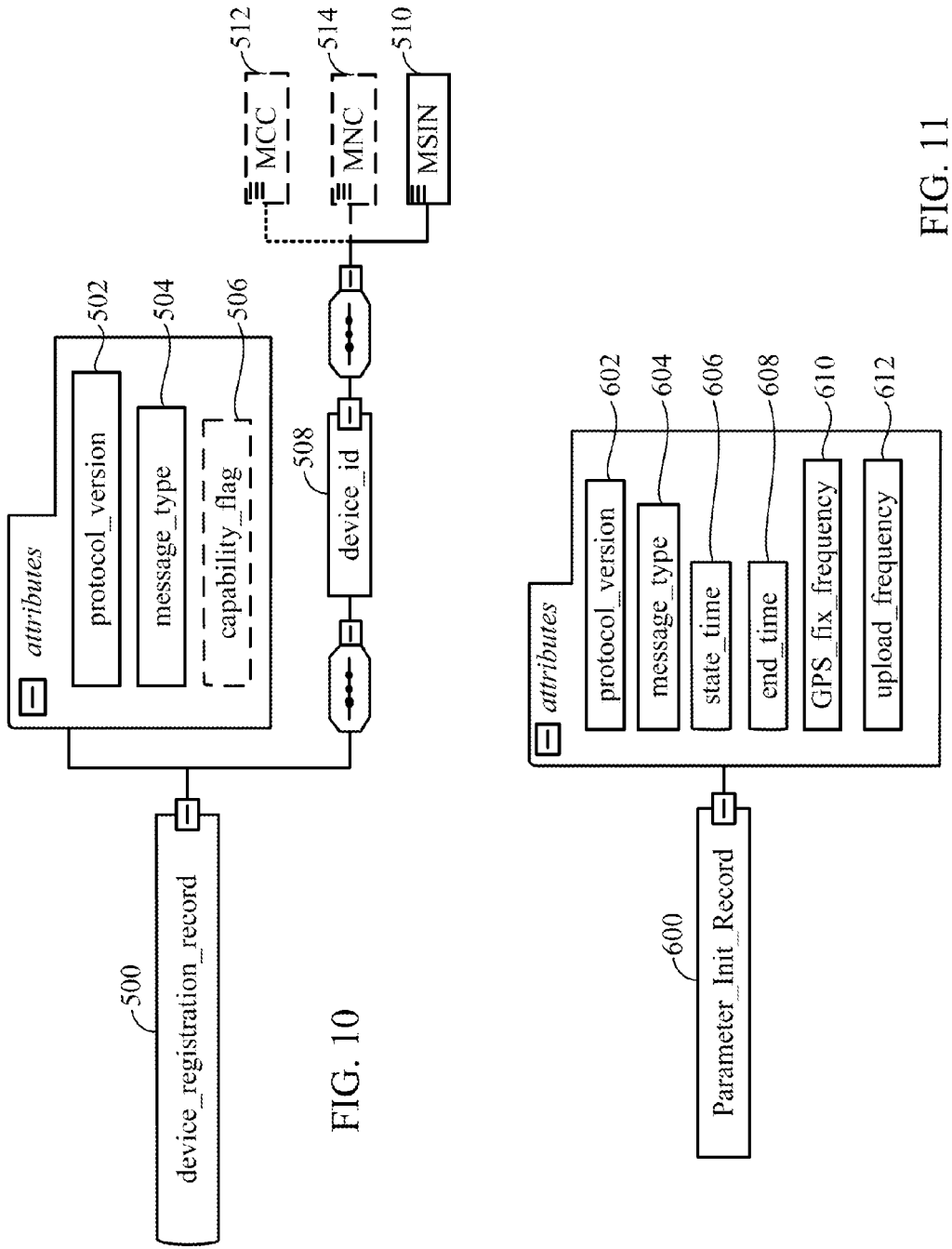

METHODS AND APPARATUS FOR APPLYING TACTILE PRESSURE SENSORS

BACKGROUND

1. Field

The following description relates generally to applications for tactile pressure sensors and, more particularly, to an apparatus and methods for applying tactile pressure sensors, obtaining data from the sensors, and providing the data to a user.

2. Background

Tactile pressure sensors measure a touch pressure. The technology has been successfully applied in touch screens. Other applications may also benefit from the use of the tactile pressure sensor technology. There is a current need in the art for the use of the tactile pressure sensor technology in other applications, such as in sport, health, and automotive applications.

SUMMARY

In an aspect of the disclosure, a method, a computer program product, and an apparatus for wireless communication is provided in which configuration information is transmitted to a tactile pressure sensor apparatus, pressure sensor data is received from the tactile pressure sensor apparatus based on the configuration information, and the received tactile pressure sensor data is provided to a user.

In an aspect of the disclosure, a system for obtaining and providing pressure feedback information includes an apparatus, a user equipment, and a server. The apparatus includes a plurality of embedded tactile pressure sensors and a transceiver for transmitting pressure sensor data from the tactile pressure sensors. The user equipment includes a transceiver for receiving the pressure sensor data from the apparatus and for transmitting the pressure sensor data. The server is for receiving the pressure sensor data from the user equipment.

In an aspect of the disclosure, an apparatus for wireless communication includes a body, a plurality of tactile pressure sensors embedded within the body on at least two opposing surfaces, a transceiver, and a processing system coupled to the transceiver and to the tactile pressure sensors. The processing system is configured to receive tactile pressure information from the tactile pressure sensors and to contact emergency services through the transceiver when the tactile pressure information indicates simultaneous activation of the tactile pressure sensors on the at least two opposing surfaces consistent with a squeezing of the body.

In an aspect of the disclosure, an apparatus for wireless communication includes a processing system, a transceiver coupled to the processing system, and a display coupled to the processing system. The processing system is configured to transmit a pressure sensor configuration including a sample rate for sampling a tactile pressure and a transmit rate for transmitting the pressure sensor data corresponding to the sampled tactile pressure. The processing system is further configured to receive pressure sensor data at the transmit rate and sampled at the sample rate, the pressure sensor data including a plurality of sampled tactile pressures and time stamps associated with the sampled tactile pressures. The processing system is further configured to process the received pressure sensor data. The processing system is further configured to display the processed data on the display.

In an aspect of the disclosure, an apparatus for wireless communication includes a surface on which a pressure can be exerted, a plurality of pressure sensors embedded in the surface, a controller coupled to the pressure sensors, and a transceiver coupled to the controller. The controller is configured to receive a pressure sensor configuration including a sample rate for sampling a tactile pressure and a transmit rate for transmitting the pressure sensor data corresponding to the sampled tactile pressure. The controller is further configured to obtain pressure sensor data from the pressure sensors. The controller is further configured to transmit the pressure sensor data and an associated time stamp to a user equipment.

BRIEF DESCRIPTION OF DRAWINGS

FIG. 9 is a diagram illustrating a message format between the pressure sensor device and the UE.

FIG. 10 is a diagram illustrating a device registration message.

FIG. 11 is a diagram illustrating a data upload parameter initialization message.

DETAILED DESCRIPTION

Various aspects of the novel systems, apparatus and methods are described more fully hereinafter with reference to the accompanying drawings. The teachings disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that that the scope of disclosure is intended to cover any aspect of the novel systems, apparatus and methods disclosed herein, whether implemented independently of or combined with any other aspect of the invention. For example, an apparatus may be implemented or a method may be practiced using any number of the aspects set forth herein. In addition, the scope of the invention is intended to cover such an apparatus or method which is practiced using other structure, functionality, or structure and functionality in addition to or other than the various aspects of the invention set forth herein. It should be understood that any aspect disclosed herein may be embodied by one or more elements of a claim.

Examples of apparatuses suitable for incorporating various aspects of the invention include, but are not limited to, a UE capable of operating in a wireless network. A UE may be referred to as a mobile phone, user terminal, wireless terminal, a mobile station, a mobile device, a subscriber station, a wireless device, a terminal, an access terminal, a node, a handheld device, or some other suitable terminology. The various concepts described throughout this disclosure are intended to apply to all suitable apparatuses regardless of their specific nomenclature.

Figure 1:
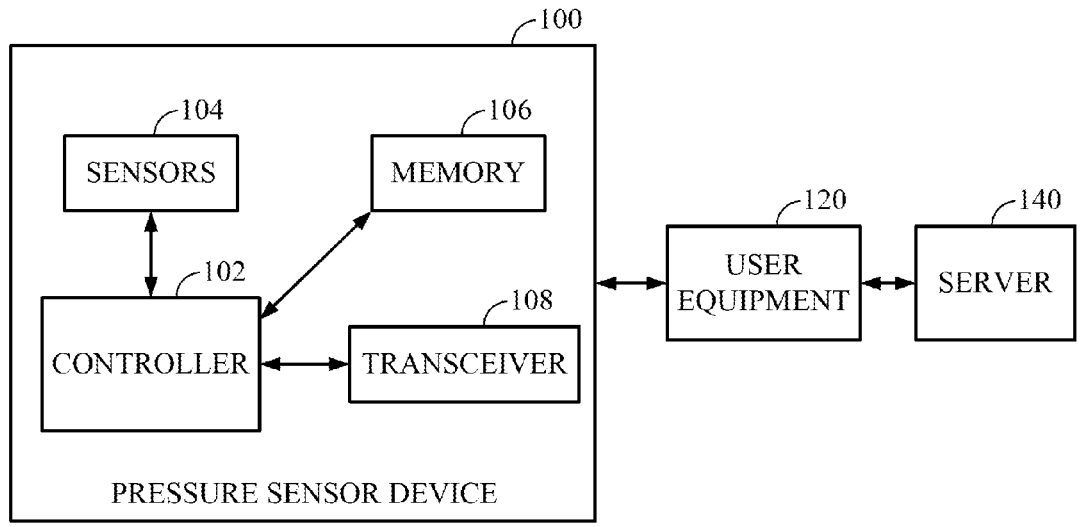
FIG. 1 is a block diagram illustrating an exemplary hardware configuration.

Various aspects of an apparatus will now be presented with reference to FIG. 1. FIG. 1 is a block diagram illustrating an exemplary hardware configuration. As shown in FIG. 1, a pressure sensor device 100 is in communication with the UE 120 and the UE 120 is in communication with the server 140. The pressure sensor device 100 includes a controller/processor 102, tactile pressure sensors 104 coupled to the controller 102, memory 106 coupled to the controller 102, and a transceiver 108 coupled to the controller 102. The tactile pressure sensors 104 provide pressure data to the controller 102. The controller 102 stores the information in memory 106. When the pressure sensor device 100 receives a request from the UE 120 for data, the pressure sensor device 100 transmits the data to the UE 120 using low power radio, such as, for example, with Bluetooth®, Bluetooth® low energy technology, Zigbee™, or ANT. Bluetooth® is a registered trademark of Bluetooth Special Interest Group (SIG). Zigbee™ is a trademark of the Zigbee Alliance.

The pressure sensor device 100 may be inserted within an apparatus for obtaining pressure measurements related to the use of the apparatus. For example, in sport applications, the sensors 104 may be layered and embedded into soles of shoes and the remaining pressure sensor device 100 embedded within or otherwise located on each shoe. That is, the sensors 104 may be layered and embedded into an insertable sole of a shoe or layered and embedded within the shoe itself, below the location of the insertable sole. The remaining pressure sensor device 100 is coupled to the sensors 104 and may be located within or outside the shoe such that it is not a hindrance to the user.

Figure 2:
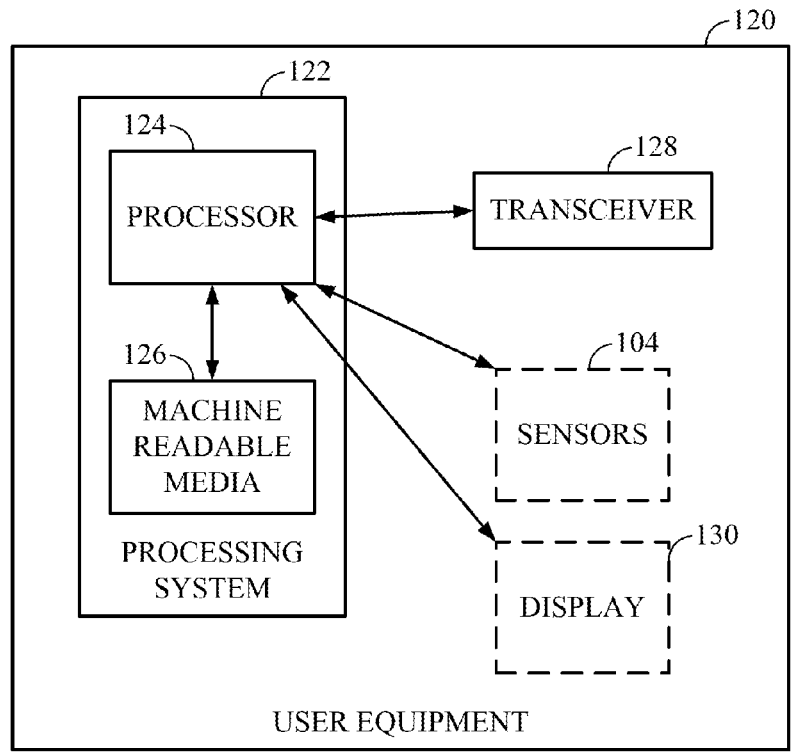
FIG. 2 is a block diagram of a user equipment (UE).

FIG. 2 is a block diagram of the UE 120. The UE 120 includes a processor 124, machine-readable media (memory) 126 coupled to the processor 124, and a transceiver 128 coupled to the processor 124. The UE 120 is able to communicate via low power radio with the pressure sensor device 100 and via an air interface with a base station, which relays received data to the server 140. In one configuration, the UE 120 is a hub for collecting the data from the pressure sensor device 100 and for relaying the data to the server 140. In another configuration, the UE 120 is a cell phone and includes a display 130. In such a configuration, the UE 120 may display the collected data to the user via the display 130.

In another configuration, the UE 120 further includes tactile pressure sensors 104. In such a configuration, the UE 120 may not communicate with a remote pressure sensor device 100, but rather, obtains input from the tactile pressure sensors 104 within the UE 120 and relays information corresponding to the input to the server 140, or otherwise, initiates an emergency call to emergency services. In such a configuration, the tactile pressure sensors 104 may serve as an emergency trigger mechanism. A number of cell phones provide an emergency button so that users, typically elderly users, may initiate an emergency call (e.g., 911, a caregiver, or an emergency service). However, activation of the emergency button may be difficult due to difficulty in locating the button in an emergency or may be delayed due to the flip-phone configuration. In an exemplary configuration, the tactile pressure sensors 104 are located on the UE 120 so that a user may squeeze the UE 120 to initiate an emergency call. In such a configuration, the tactile pressure sensors may be embedded within the body of the UE 120 on at least two opposing surfaces so that simultaneous activation of the tactile pressure sensors consistent with a squeezing of the body may initiate the emergency call.

Referring again to FIG. 2, the processor 124 and the machine-readable media 126 may together be referred to as a processing system 122. However, the processing system 122 may include the processor 124 without the machine-readable media 126 for certain processor 124 configurations. The processing system 122 may include one or more processors. The one or more processors may be implemented with any combination of general-purpose microprocessors, microcontrollers, a Digital Signal Processors (DSP), Field Programmable Gate Arrays (FPGA), Programmable Logic Devices (PLD), controllers, state machines, gated logic, discrete hardware components, or any other suitable entities that can perform calculations or other manipulations of information.

The processing system 122 may also include the machine-readable media 126 for storing software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the one or more processors, cause the processing system 122 to perform the various functions described below, as well as other protocol processing functions.

The machine-readable media 126 may include storage integrated into one or more of the processors. The machine-readable media 126 may also include storage external to the one or more processor, such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device. In addition, the machine-readable media 126 may include a transmission line or a carrier wave that encodes a data signal. Those skilled in the art will recognize how best to implement the described functionality for the processing system.

Figure 3:
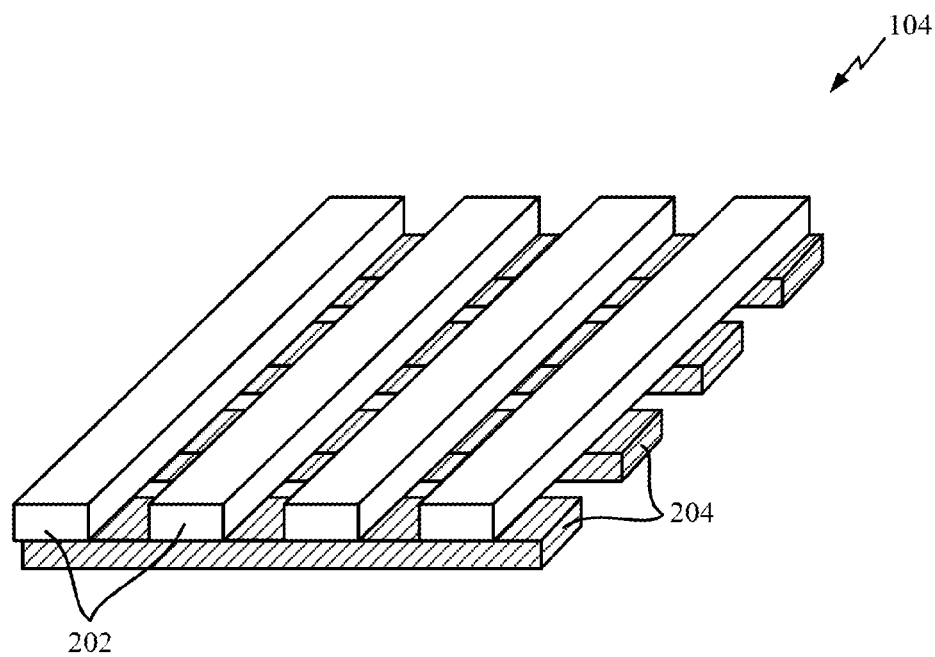
FIG. 3 is a diagram of a grid of tactile pressure sensors.

FIG. 3 is a diagram of a grid of tactile pressure sensors 104. The tactile pressure sensors 104 are layered in a grid, with electrodes 202 extending in columns and overlapping the electrodes 204 extending in rows. Capacitors are formed at the overlapping portions, with the capacitance equal to the area of the overlap divided by the distance between the electrodes 202, 204. The capacitance is measured by selecting one of the row electrodes 204 and one of the column electrodes 202.

Figure 4:
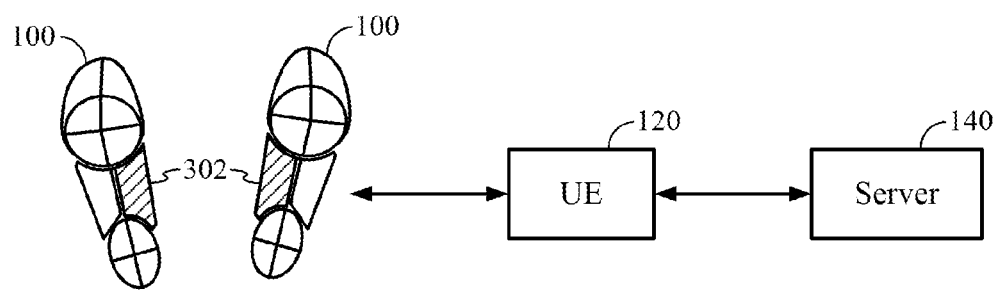
FIG. 4 is a diagram of soles with the tactile pressure sensors.

FIG. 4 is a diagram of soles with the tactile pressure sensors. As mentioned supra, the pressure sensor device 100 may be embedded in the soles 302 of shoes or boots. Such a configuration may be used in sport applications such as cycling, golfing, skiing, and running to measure an athlete's performance, such as power, balance, and cadence. The UE 120 may be configured to obtain GPS information and to associate the GPS information with the data from the pressure sensor device 100 in order to correlate velocity, acceleration, and elevation information with the pressure data.

Figure 5:
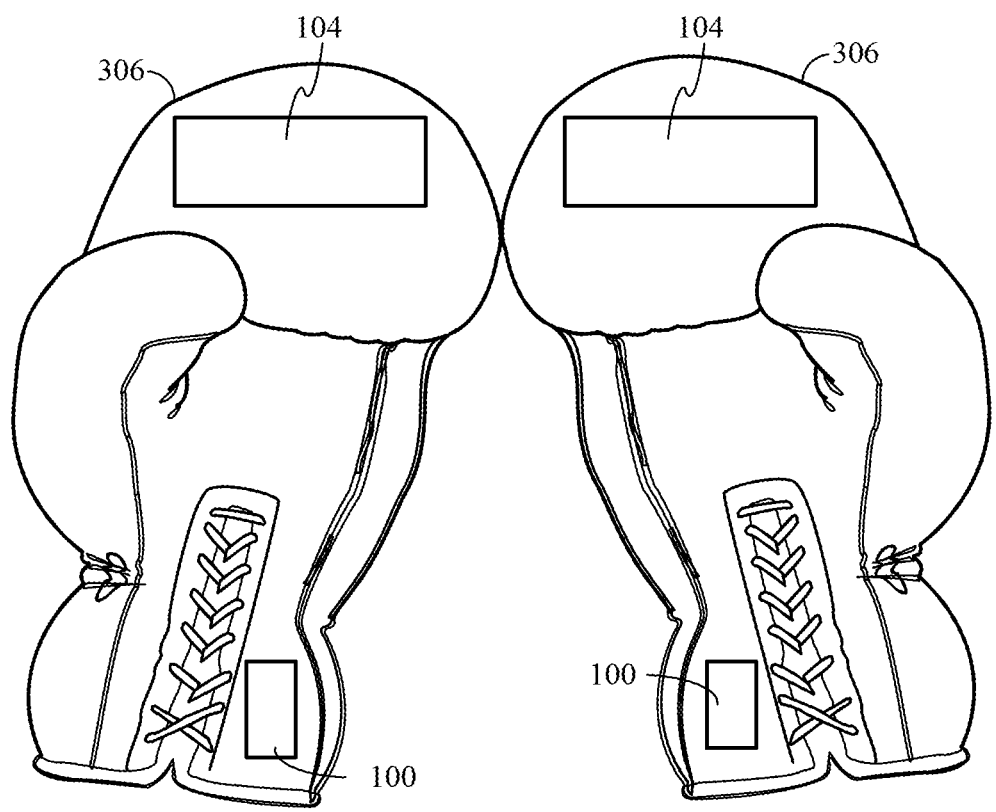
FIG. 5 is a diagram of boxing gloves with tactile pressure sensors.

FIG. 5 is a diagram of boxing gloves 306 with the pressure sensor device 100. The pressure sensor device 100 may be embedded in boxing gloves 306, with the tactile pressure sensors 104 located in the knuckle areas of the gloves and the remaining components of the pressure sensor device 100 located near the wrist or other non-contact portions of the boxing gloves. In such a configuration, the pressure sensor device can provide feedback on the force of impact of a punch, thereby providing athletes with valuable training information or judges with information on whether a punch has landed.

The pressure sensor device 100 may be utilized in other applications, such as, for example, within an exercise tool for arthritis, such as a squeeze ball. The exercise tool may be layered with the tactile pressure sensors 104 and offload the data from the tactile pressure sensors 104 using low power radio in order to report and to analyze the user's grip, strength, dexterity, mobility, and motor skills. As discussed supra, the data may be offloaded to the UE 120, such as a cell phone, and analyzed in real time on the cell phone. Alternatively or in addition, the data may be offloaded to the server 140 and analyzed via the Internet. The server 140 is configured to process the offloaded data with previously received sensor data in order to obtain trend information. The server 140 provides the trend information to the user.

The pressure sensor device 100 may also be utilized in a walking cane to diagnose the user's walking pattern, such as whether the user is leaning forward or leaning to a side. In such a configuration, the pressure sensors may be positioned on a bottom surface of the walking cane to detect the walking and leaning patterns of the user. The information from the pressure sensors can be provided to a physician to diagnose for an early sign of a potential likelihood of falling.

The pressure sensor device 100 may also be utilized in helmets, such as football helmets, to predict a likelihood of concussion if the pressure data includes a pressure greater than a particular threshold. In such a configuration, the tactile pressure sensors may be layered on an inner surface of the helmet. The data from the helmet can be offloaded to the UE 120 and then to the server 140, where it may be analyzed to determine whether to evaluate a particular player.

The pressure sensor device 100 may also be utilized in automotive applications, such as to monitor driver behavior. Statistics show driver distraction is the greatest cause of automobile accidents. One sign of drivers being distracted is that their hands are not gripping the steering wheel properly. Specifically, the pressure sensor device 100 may be utilized with a steering wheel to detect for a change in a user's grip and to detect whether one hand or two hands make full contact with the steering wheel, as one-handed driving could indicate that the driver is text messaging or using the other hand for non-driving purposes. Furthermore, contact with less than one hand only, such as a single finger, could indicate potentially unsafe driving habits. In such a configuration, the tactile pressure sensors 104 may be embedded within the steering wheel in areas that a driver would grip when steering the vehicle. The data from the tactile pressure sensors 104 may be relayed to the UE 120 via a wireless signal or wireline, and then sent to a Fleet Management Control Center. The data may be utilized at the center to alert the driver.

Such an application may also be utilized for non-commercial automobiles to monitor new or teenage drivers for reckless behavior, such as taking the hands off the steering wheel. The information may be gathered by an insurance company for risk analysis and assessment for plan coverage.

Figure 6:
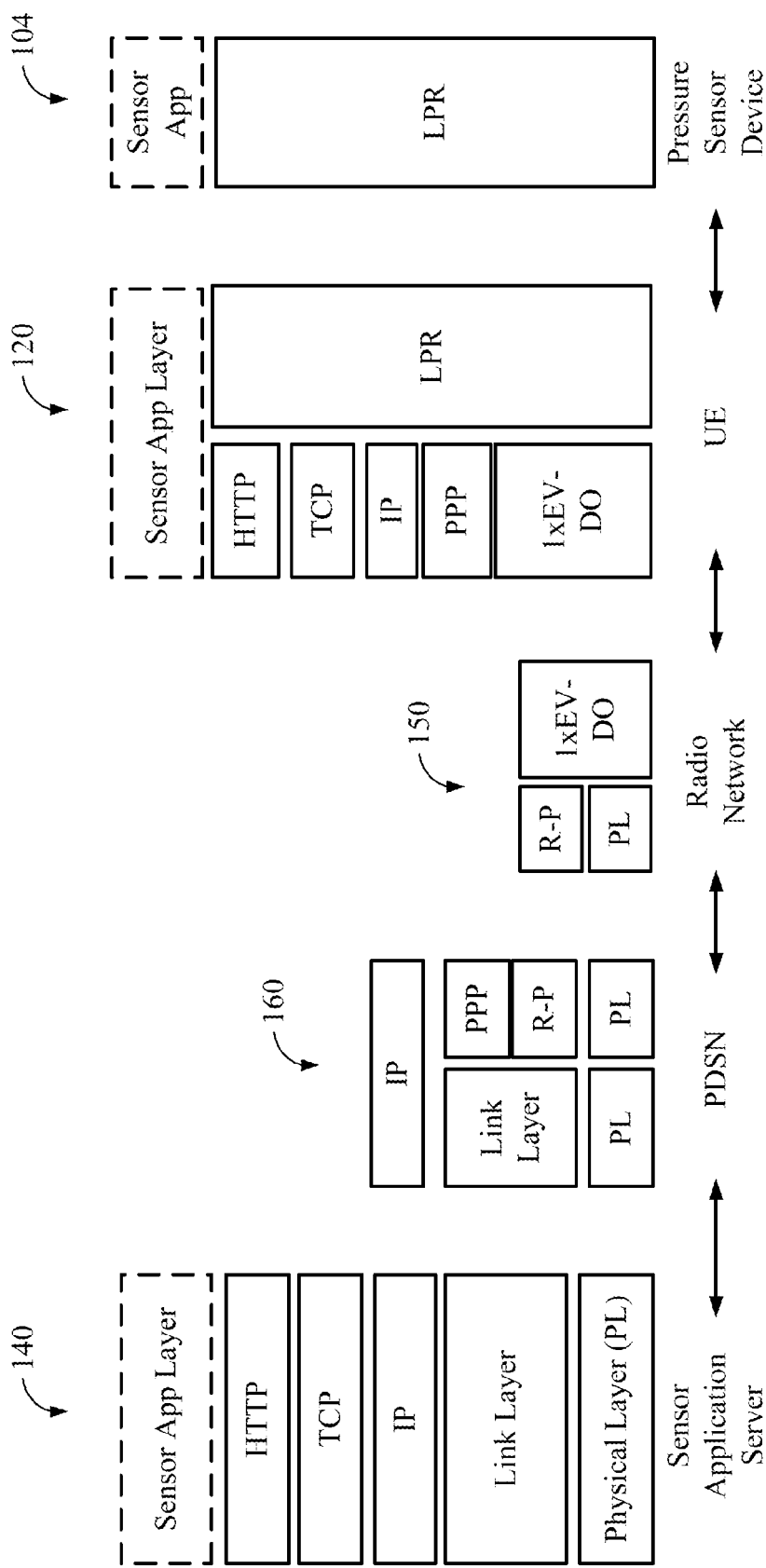
FIG. 6 is a block diagram illustrating a protocol architecture including the pressure sensor device and the UE.

FIG. 6 is a block diagram illustrating a protocol architecture including the pressure sensor device 100 and the UE 120. As shown in FIG. 6, the pressure sensor device 100 includes a low power radio (LPR) component and the sensor application 104. The pressure sensor device 100 communicates with the UE 120, which communicates with the sensor application server 140 via the radio network 150 and the Packet Data Serving Node (PDSN) 160.

Figure 7:
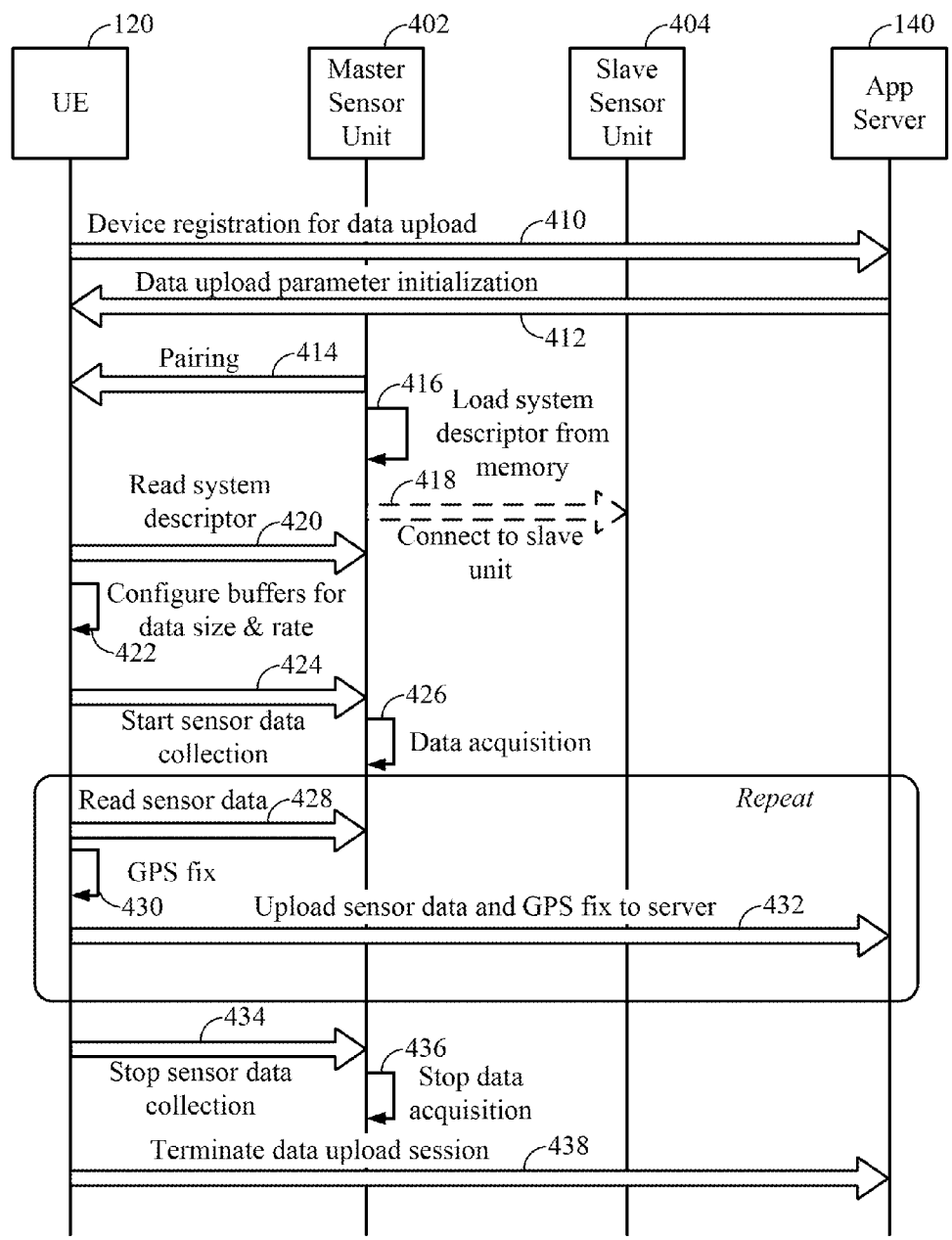
FIG. 7 is a diagram illustrating the system message flow sequence.

FIG. 7 is a diagram illustrating the system message flow sequence. As shown in FIG. 7, there are two pressure sensor devices 100, one that is a master 402 and another that is a slave 404. Such a configuration is applicable to the sole application with one sole being embedded with a pressure sensor device configured to be the master 402 and the other sole being embedded with a pressure sensor device configured to be the slave 404. The UE 120 first registers for data upload (410). Next, the Application Sever 140 initializes the data upload parameters (412). Next, the UE 120 pairs with the master sensor unit 402 (414). The master sensor unit 402 loads the system descriptor from memory (416). The master sensor unit 402 connects to the slave unit (418). The UE 120 reads the system descriptor (420). The UE 120 configures buffers for the data size and data rate (422). The UE 120 then starts sensor data collection (424). The master sensor unit 402 acquires data from the sensors (426) in the master sensor unit 402 and slave sensor unit 404. The UE 120 reads the sensor data (428). The UE 120 may also perform GPS fixes (430). The UE 120 uploads the sensor data and GPS data to the Application Server 140 (432). Steps 428 through 432 may be repeated. The UE 120 may perform the GPS fixes with a different periodicity than the periodicity in which the UE 120 reads the sensor data. Subsequently, the UE 120 stops sensor data collection (434), the master stops data acquisition (436), and the UE 120 informs the Application Server 140 that it is terminating the data upload session (438).

Figure 8:
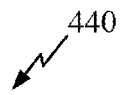
FIG. 8 is a diagram illustrating a configuration of the system descriptor message.

FIG. 8 is a diagram illustrating a configuration of the system descriptor message 440. Byte 0 defines the transmit rate in units of 0.1 Hz, byte 1 the sample rate in units of 0.5 Hz, and bytes 2 through 9 the sensor sizes. The system descriptor message 440 is sent by the master sensor unit 402 to the UE 120 in step 420 (FIG. 7). The system descriptor message 440 informs the UE 120 of the transmit rate, the sample rate, and the sensor sizes of the master and slave sensor units 402, 404. As indicated in FIG. 8, four sensors are assumed in each of the master and slave sensor units 402, 404, thus the system descriptor message has a fixed size of 10 bytes. If no slave is present, sensors 4-7 will report a zero size. The sensor size defines the size of a particular sensor in the master and slave sensor units 402, 404 and is given as a number of elements, with each element being two bytes long. The maximum frame size is 24 elements per unit (48 total with master and slave) regardless of the number of devices configured. The sample rate range is 0.5-100 Hz and the transmit rate range is 0.1-25 Hz.

FIG. 9 is a diagram illustrating a message format between the pressure sensor device 100 and the UE 120 utilized in step 428 (FIG. 7). As shown in FIG. 9, each data frame includes an 11-byte header, including a header (two bytes), version, device type, device ID, frame counter, system status, and a timestamp with an accuracy to 1 ms (4 bytes). The header byte may be set to 0xFF, which cannot naturally appear in data and so it can be used to identify the start of the message. The device type and device ID can identify a category and subcategory, respectively. For example, the device type can be boxing and the device ID can be helmet or gloves. The frame counter is the frame number and is used to detect dropped frames. The system status is the status of the system such as the slave link state (i.e., loss of slave unit) or whether there have been hardware errors. The data follows the 11-byte header. The data includes data from each sensor, including slave devices. If the connection to a slave is lost, zeros are returned for its data. After the data is a checksum. As shown, the checksum is 8 bits, but could be larger, such as 16 bits. The checksum can be an 8-bit or 16-bit cyclic redundancy check (CRC).

FIG. 10 is a diagram illustrating a device registration message 500, which is utilized in step 410 (FIG. 7). The device registration message 500 is used by the UE 120 to register with the server 140 for data upload. The message 500 includes a protocol version 502, message type 504, a device ID 508, and may additionally include a capability flag 506. The protocol version 502 specifies the current protocol version. The message type 504 identifies the message type being used. The capability flag 506 identifies a wireless, hardware, and software capability of the device. The device ID 508 is a unique device identifier. If the UE 120 is a mobile station (i.e., cell phone), the device ID 508 includes the mobile station identification number (MSIN) 510, and may additionally include the mobile country code (MCC) 512 and the mobile network code (MNC) 514.

FIG. 11 is a diagram illustrating a data upload parameter initialization message 600, which is utilized in step 412 (FIG. 7). The data upload parameter initialization message 600 is sent from the server 140 to the UE 120. The message 600 includes a protocol version 602, a message type 604, a start time 606, an end time 608, a GPS fix frequency 610, and an upload frequency 612. The protocol version 602 specifies the current protocol version. The message type 604 identifies the message being used. The start time 606 is the time to start uploading data. The end time 608 is the time to stop uploading data. The GPS fix frequency 610 is the frequency which GPS fixes should be taken. The upload frequency 612 is the frequency at which the data should be uploaded to the application server.

The data upload parameter initialization message 600 allows the server 140 to request when data should be collected, the frequency of upload, whether GPS fixes should accompany the sensor data, and the frequency of the GPS fixes. When the GPS frequency is set to zero, no GPS fixes are performed. In such a configuration, the battery life for the pressure sensor device 100 may be preserved, as the server 140 can effectively control the battery usage through the parameters in the message 600.

Figure 12:
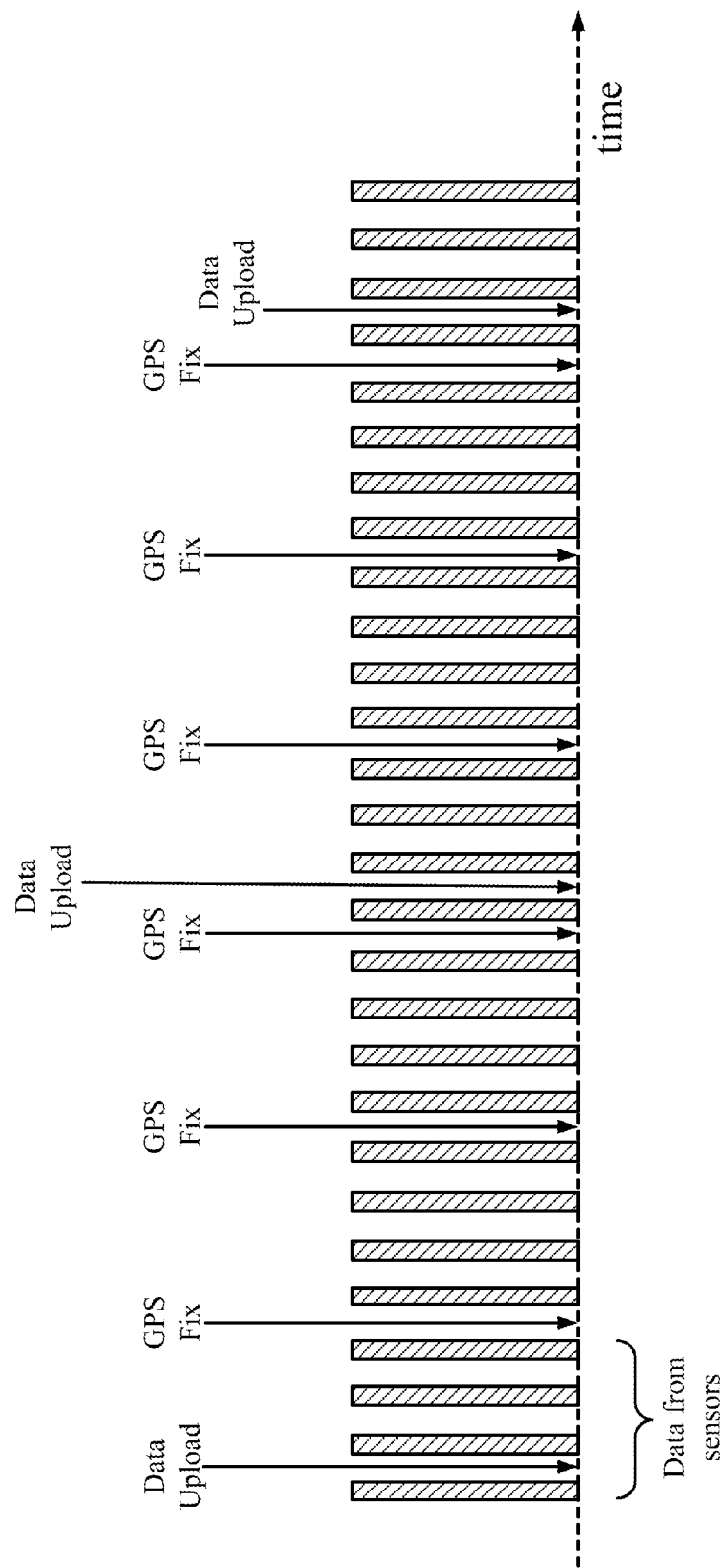
FIG. 12 is a diagram illustrating data upload scenarios.

FIG. 12 is a diagram illustrating data upload scenarios. Depending on the frequency of data upload and GPS fix, each data upload may contain multiple frames of data from the sensors and a number of GPS fixes. As shown in FIG. 12, the sensor and GPS data is uploaded with a frequency of once every twelve frames and the GPS fix is performed once every four frames. A bundle may be defined as the number of frames between GPS fixes, which in this example, is four.

Figure 13:
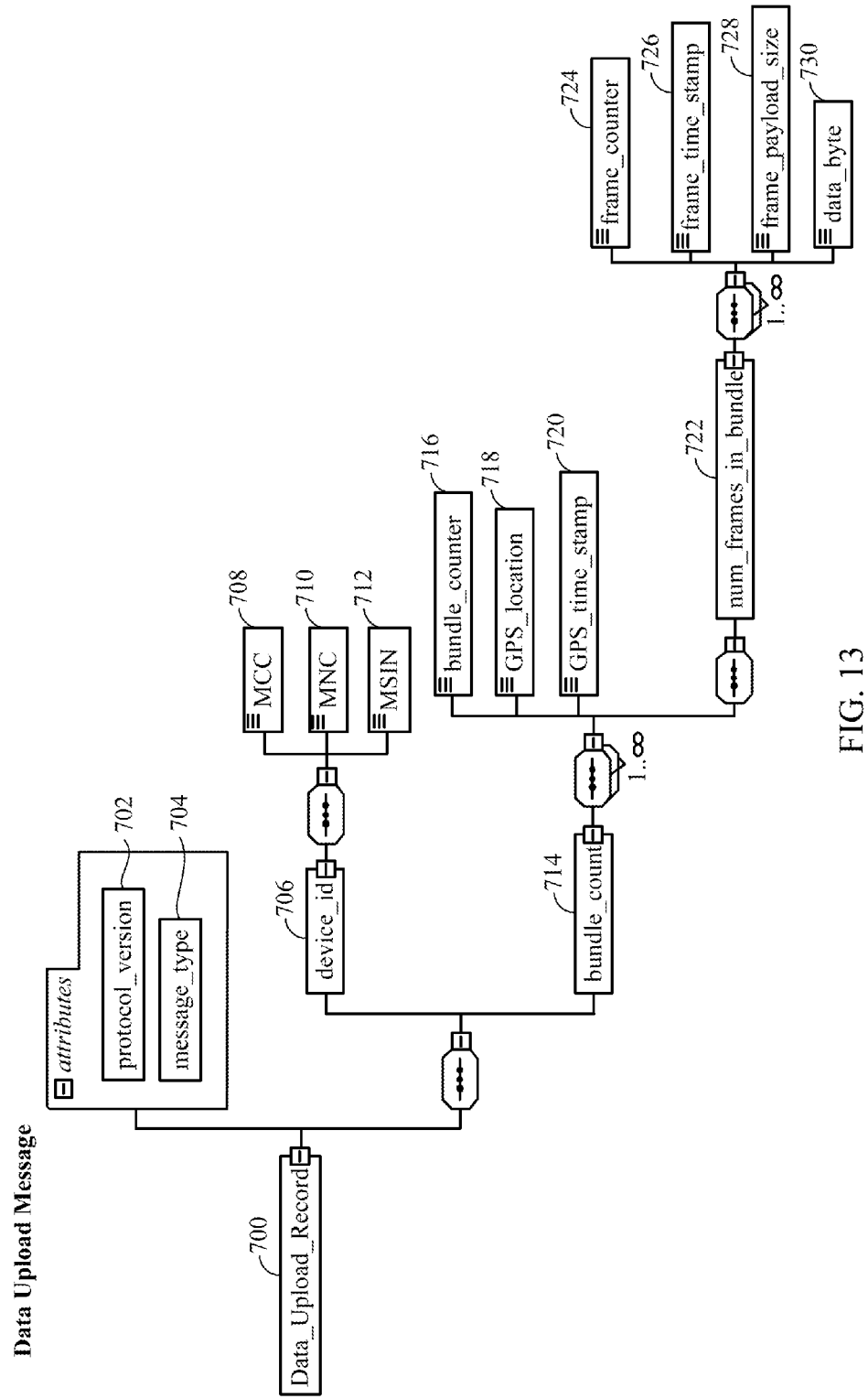
FIG. 13 is a diagram illustrating a data upload message.

FIG. 13 is a diagram illustrating a data upload message 700, which is utilized in step 432 (FIG. 7). The data upload message 700 includes a protocol version 702, a message type 704, a device ID 706, and a bundle count 714. The device ID 706 includes an MCC 708, an MNC 710, and an MSIN 712. The bundle count 714 includes a bundle counter 716, a GPS location 718, a GPS time stamp 720, and the number of frames in the bundle 722. The number of frames in the bundle 722 includes a frame counter 724, a frame time stamp 726, a frame payload size 728, and the data 730. The bundle counter 716 is the bundle number. The GPS location 718 is the GPS fix for the given bundle, the GPS time stamp 720 is the time when the GPS fix was taken, the frame counter 724 is the frame number of the bundle, and the frame payload size 728 is the size of the frame.

Referring again to FIG. 1 and FIG. 2, as discussed supra, a system for obtaining and providing pressure feedback information includes the apparatus 100, the UE 120, and the server 140. The apparatus 100 includes a plurality of embedded tactile pressure sensors 104 and a transceiver 108 for transmitting pressure sensor data from the tactile pressure sensors 104. The UE 120 includes a transceiver 128 for receiving the pressure sensor data from the apparatus 100 and for transmitting the pressure sensor data. The server 140 receives the pressure sensor data from the UE 120.

In one configuration, the UE 120 further includes a processing system 122 and a display 130. The processing system 122 is configured to process the received pressure sensor data and to display the processed data on the display 130 for a user as the pressure sensor data is being received from the apparatus 100. In one configuration, the server 140 is configured to process the pressure sensor data with previous pressure sensor data in order to obtain trend information and is configured to provide the trend information to a user.

In one configuration, the apparatus 100 is a helmet and the tactile pressure sensors 104 are layered on an inner surface of the helmet to detect an impact force on the inner surface. In one configuration, the apparatus 100 is a steering wheel and the tactile pressure sensors 104 are positioned on the steering wheel to detect whether one hand or two hands make full contact with the steering wheel. In one configuration, the apparatus 100 is a walking cane and the tactile pressure sensors 104 are positioned on a bottom surface of the walking cane to detect walking and leaning patterns of a user using the walking cane. In one configuration, the apparatus 100 is a boxing glove and the tactile pressure sensors 104 are positioned on an impact surface of the boxing glove to detect an impact force on the impact surface. In one configuration, the apparatus 100 is a sole and the tactile pressure sensors 104 are positioned on the sole to detect cadence and leaning patterns of a user. In one configuration, the apparatus 100 is a squeeze ball and the tactile pressure sensors 104 are layered on a surface of the squeeze ball to detect a squeeze strength of a user. The apparatus may be other types of equipment, such as, for example, a gripping ball that may be gripped by a pitcher so that the pitcher can practice particular grips and ascertain whether he or she has an appropriate grip on the ball for a particular type of pitch.

In one configuration, the UE 120 is configured to transmit and the apparatus 100 is configured to receive a pressure sensor configuration including a sample rate for sampling a tactile pressure and a transmit rate for transmitting the pressure sensor data corresponding to the sampled tactile pressure. In one configuration, the apparatus 100 is configured to transmit and the UE 120 is configured to receive the pressure sensor data using low power radio. In one configuration, the apparatus 100 is configured to transmit and the UE 120 is configured to receive the pressure sensor data with an associated time stamp. In one configuration, the UE 120 is configured to receive a GPS signal, to determine GPS locations based on the GPS signal, to associate the GPS locations with the received pressure sensor data, and to transmit the GPS locations with the associated pressure sensor data to the server 140. In one configuration, the server 140 is configured to correlate the GPS locations with the associated pressure sensor data to obtain velocity, acceleration, and elevation information as related to the associated pressure sensor data. In one configuration, the server 140 is configured to send a request to the UE 120 with information on when the pressure sensor data should be collected by the apparatus 100, a frequency of upload by the apparatus 100, whether the UE 120 should obtain GPS coordinates in association with the received pressure sensor data, and a frequency that the UE 120 should obtain the GPS coordinates.

The UE 120 for wireless communication may include a body, a plurality of tactile pressure sensors 104 embedded within the body on at least two opposing surfaces, a transceiver 128, and a processing system 122 coupled to the transceiver 128 and to the tactile pressure sensors 104. The processing system 122 may be configured to receive tactile pressure information from the tactile pressure sensors 104 and to contact emergency services through the transceiver 128 when the tactile pressure information indicates simultaneous activation of the tactile pressure sensors 104 on the at least two opposing surfaces consistent with a squeezing of the body.

In one configuration, the UE 120 for wireless communication includes a processing system 122, a transceiver 128 coupled to the processing system 122, and a display 130 coupled to the processing system 122. The processing system 122 is configured to transmit a pressure sensor configuration including a sample rate for sampling a tactile pressure and a transmit rate for transmitting the pressure sensor data corresponding to the sampled tactile pressure; to receive pressure sensor data at the transmit rate and sampled at the sample rate, the pressure sensor data including a plurality of sampled tactile pressures and time stamps associated with the sampled tactile pressures; to process the received pressure sensor data; and to display the processed data on the display 130.

In one configuration, the processing system 122 is further configured to receive a GPS signal, to determine a GPS location based on the GPS signal, to associate the GPS location with the received pressure sensor data, and to transmit the GPS location with the associated pressure sensor data to a server 140. In one configuration, the processing system 122 is configured to receive the pressure sensor data through low power radio.

In one configuration, the apparatus 100 for wireless communication includes a surface on which a pressure can be exerted, a plurality of pressure sensors 104 embedded in the surface, a controller 102 coupled to the pressure sensors 104, and a transceiver 108 coupled to the controller 102. The controller 102 is configured to receive a pressure sensor configuration including a sample rate for sampling a tactile pressure and a transmit rate for transmitting the pressure sensor data corresponding to the sampled tactile pressure; to obtain pressure sensor data from the pressure sensors 104; and to transmit the pressure sensor data and an associated time stamp to the UE 120.

In one configuration, the apparatus 100 is a sole, a shoe, a boot, a helmet, a boxing glove, a cane, a squeeze ball, and a steering wheel. The apparatus 100 may be other equipment if there would be some benefit to a user in knowing a pressure applied to a surface of the equipment.

Figure 14:
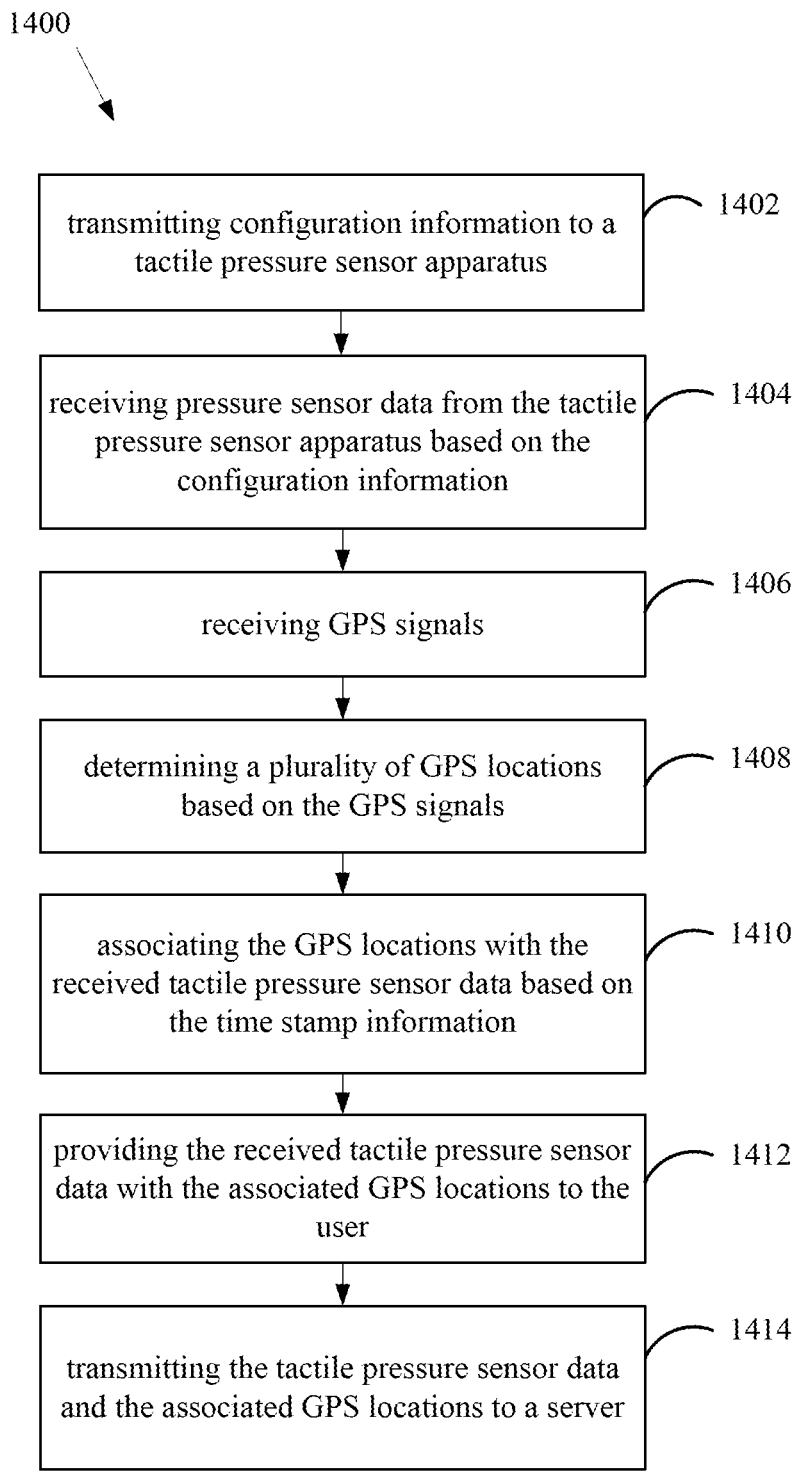
FIG. 14 is a flowchart of an exemplary method.

FIG. 14 is a flowchart of an exemplary method. The method includes transmitting configuration information to a tactile pressure sensor apparatus (1402) and receiving pressure sensor data from the tactile pressure sensor apparatus based on the configuration information (1404). In one configuration, the configuration information includes a sample rate for sampling a tactile pressure and a transmit rate for transmitting the tactile pressure sensor data corresponding to the sampled tactile pressure. In one configuration, the tactile pressure sensor data includes a plurality of sampled tactile pressures sampled at the sample rate and time stamp information associated with the sampled tactile pressures. In one configuration, the pressure sensor data is received at the transmit rate. In one configuration, the method further includes receiving GPS signals (1406), determining a plurality of GPS locations based on the GPS signals (1408), associating the GPS locations with the received tactile pressure sensor data based on the time stamp information (1410), and providing the received tactile pressure sensor data with the associated GPS locations to the user (1412). In one configuration, the method further includes transmitting the tactile pressure sensor data and the associated GPS locations to a server (1414). In one configuration, the tactile pressure sensor data is received through low power radio. In one configuration, the low power radio is one selected from the group consisting of Bluetooth, Bluetooth low energy, ZigBee, and ANT.

Figure 15:
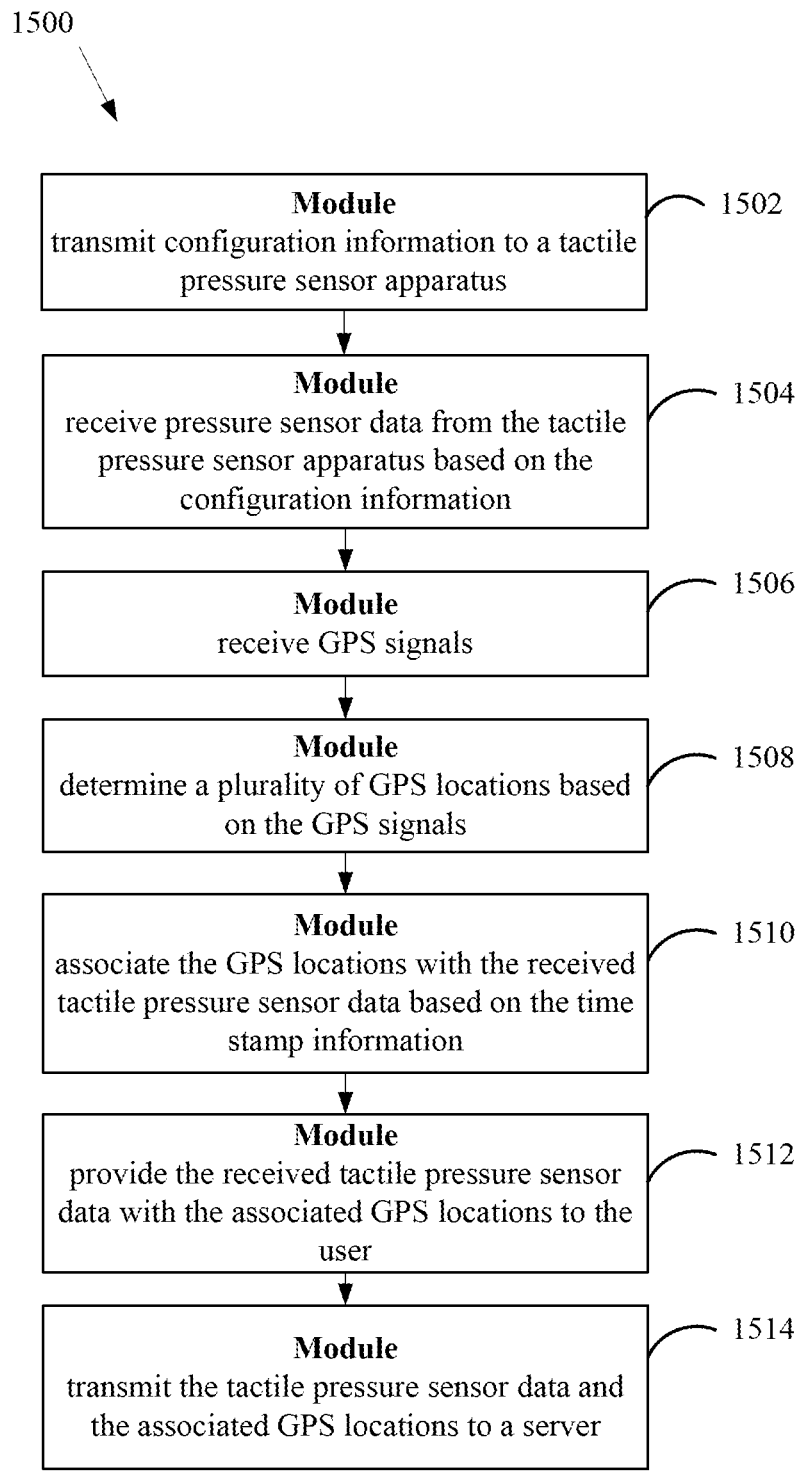
FIG. 15 is a block diagram illustrating the functionality of an exemplary apparatus.

FIG. 15 is a block diagram illustrating the functionality of an exemplary apparatus 120. The exemplary apparatus 120 includes a module 1502 that transmits configuration information to a tactile pressure sensor apparatus and a module 1504 that receives pressure sensor data from the tactile pressure sensor apparatus based on the configuration information. In one configuration, the configuration information includes a sample rate for sampling a tactile pressure and a transmit rate for transmitting the tactile pressure sensor data corresponding to the sampled tactile pressure. In one configuration, the tactile pressure sensor data includes a plurality of sampled tactile pressures sampled at the sample rate and time stamp information associated with the sampled tactile pressures. In one configuration, the pressure sensor data is received at the transmit rate. In one configuration, the exemplary apparatus 120 further includes a module 1506 that receives GPS signals, a module 1508 that determines a plurality of GPS locations based on the GPS signals, a module 1510 that associates the GPS locations with the received tactile pressure sensor data based on the time stamp information, and a module 1512 that provides the received tactile pressure sensor data with the associated GPS locations to the user. In one configuration, the exemplary apparatus 120 further includes a module 1514 that transmits the tactile pressure sensor data and the associated GPS locations to a server. In one configuration, the tactile pressure sensor data is received through low power radio. In one configuration, the low power radio is one selected from the group consisting of Bluetooth, Bluetooth low energy, ZigBee, and ANT.

In one configuration, the apparatus 120 for wireless communication includes means for transmitting configuration information to a tactile pressure sensor apparatus, means for receiving pressure sensor data from the tactile pressure sensor apparatus based on the configuration information, and means for providing the received tactile pressure sensor data to a user. In one configuration, the apparatus 120 further includes means for receiving GPS signals, means for determining a plurality of GPS locations based on the GPS signals, means for associating the GPS locations with the received tactile pressure sensor data based on the time stamp information, and means for providing the received tactile pressure sensor data with the associated GPS locations to the user. In one configuration, the apparatus 120 further includes means for transmitting the tactile pressure sensor data and the associated GPS locations to a server. The aforementioned means is the processing system 122 configured to perform the functions recited by the aforementioned means.

The previous description is provided to enable any person skilled in the art to fully understand the full scope of the disclosure. Modifications to the various configurations disclosed herein will be readily apparent to those skilled in the art. Thus, the claims are not intended to be limited to the various aspects of the disclosure described herein, but is to be accorded the full scope consistent with the language of claims, wherein reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

The invention claimed is:

1. A method of wireless communication, comprising:
 transmitting configuration information to a tactile pressure sensor apparatus;
 receiving pressure sensor data from the tactile pressure sensor apparatus based on the configuration information; and
 providing the received tactile pressure sensor data to a user,
 wherein the configuration information comprises a sample rate for sampling a tactile pressure and a transmit rate for transmitting the tactile pressure sensor data corresponding to the sampled tactile pressure.

2. The method of claim 1, wherein the tactile pressure sensor data comprises a plurality of sampled tactile pressures sampled at the sample rate and time stamp information associated with the sampled tactile pressures.

3. The method of claim 2, wherein the pressure sensor data is received at the transmit rate.

4. The method of claim 3, further comprising:
 receiving GPS signals;
 determining a plurality of GPS locations based on the GPS signals;
 associating the GPS locations with the received tactile pressure sensor data based on the time stamp information; and
 providing the received tactile pressure sensor data with the associated GPS locations to the user.

5. The method of claim 4, further comprising transmitting the tactile pressure sensor data and the associated GPS locations to a server.

6. The method of claim 5, wherein the tactile pressure sensor data is received through low power radio.

7. The method of claim 6, wherein the low power radio is one selected from the group consisting of Bluetooth, Bluetooth low energy, ZigBee, and ANT.

8. An apparatus for wireless communication, comprising:
 means for transmitting configuration information to a tactile pressure sensor apparatus;
 means for receiving pressure sensor data from the tactile pressure sensor apparatus based on the configuration information; and
 means for providing the received tactile pressure sensor data to a user,
 wherein the configuration information comprises a sample rate for sampling a tactile pressure and a transmit rate for transmitting the tactile pressure sensor data corresponding to the sampled tactile pressure.

9. The apparatus of claim 8, wherein the tactile pressure sensor data comprises a plurality of sampled tactile pressures sampled at the sample rate and time stamp information associated with the sampled tactile pressures.

10. The apparatus of claim 9, wherein the pressure sensor data is received at the transmit rate.

11. The apparatus of claim 10, further comprising:
 means for receiving GPS signals;
 means for determining a plurality of GPS locations based on the GPS signals;
 means for associating the GPS locations with the received tactile pressure sensor data based on the time stamp information; and
 means for providing the received tactile pressure sensor data with the associated GPS locations to the user.

12. The apparatus of claim 11, further comprising means for transmitting the tactile pressure sensor data and the associated GPS locations to a server.

13. The apparatus of claim 12, wherein the tactile pressure sensor data is received through low power radio.

14. The apparatus of claim 13, wherein the low power radio is one selected from the group consisting of Bluetooth, Bluetooth low energy, ZigBee, and ANT.

15. A computer program product, comprising:
 a non-transitory computer-readable medium comprising code for:
 transmitting configuration information to a tactile pressure sensor apparatus;
 receiving pressure sensor data from the tactile pressure sensor apparatus based on the configuration information; and
 providing the received tactile pressure sensor data to a user,
 wherein the configuration information comprises a sample rate for sampling a tactile pressure and a transmit rate for transmitting the tactile pressure sensor data corresponding to the sampled tactile pressure.

16. The computer program product of claim 15, wherein the tactile pressure sensor data comprises a plurality of sampled tactile pressures sampled at the sample rate and time stamp information associated with the sampled tactile pressures.

17. The computer program product of claim 16, wherein the pressure sensor data is received at the transmit rate.

18. The computer program product of claim 17, wherein the computer-readable medium further comprises code for:
 receiving GPS signals;
 determining a plurality of GPS locations based on the GPS signals;
 associating the GPS locations with the received tactile pressure sensor data based on the time stamp information; and
 providing the received tactile pressure sensor data with the associated GPS locations to the user.

19. The computer program product of claim 18, wherein the computer-readable medium further comprises code for transmitting the tactile pressure sensor data and the associated GPS locations to a server.

20. The computer program product of claim 19, wherein the tactile pressure sensor data is received through low power radio.

21. The computer program product of claim 20, wherein the low power radio is one selected from the group consisting of Bluetooth, Bluetooth low energy, ZigBee, and ANT.

22. An apparatus for wireless communication, comprising:
 a processing system configured to:
 transmit configuration information to a tactile pressure sensor apparatus;
 receive pressure sensor data from the tactile pressure sensor apparatus based on the configuration information; and
 provide the received tactile pressure sensor data to a user,
 wherein the configuration information comprises a sample rate for sampling a tactile pressure and a transmit rate for transmitting the tactile pressure sensor data corresponding to the sampled tactile pressure.

23. The apparatus of claim 22, wherein the tactile pressure sensor data comprises a plurality of sampled tactile pressures sampled at the sample rate and time stamp information associated with the sampled tactile pressures.

24. The apparatus of claim 23, wherein the pressure sensor data is received at the transmit rate.

25. The apparatus of claim 24, wherein the processing system is further configured to:
receive GPS signals;
determine a plurality of GPS locations based on the GPS signals;
associate the GPS locations with the received tactile pressure sensor data based on the time stamp information; and
provide the received tactile pressure sensor data with the associated GPS locations to the user.

26. The apparatus of claim 25, wherein the processing system is further configured to transmit the tactile pressure sensor data and the associated GPS locations to a server.

27. The apparatus of claim 26, wherein the tactile pressure sensor data is received through low power radio.

28. The apparatus of claim 27, wherein the low power radio is one selected from the group consisting of Bluetooth, Bluetooth low energy, ZigBee, and ANT.

29. A system for obtaining and providing pressure feedback information, comprising:
an apparatus comprising a plurality of embedded tactile pressure sensors and a transceiver for transmitting pressure sensor data from the tactile pressure sensors;
a user equipment comprising a transceiver for receiving the pressure sensor data from the apparatus and for transmitting the pressure sensor data; and
a server for receiving the pressure sensor data from the user equipment;
wherein the user equipment is configured to transmit and the apparatus is configured to receive a pressure sensor configuration, and wherein the pressure sensor data is based on the configuration information.

30. The system of claim 29, wherein the user equipment further comprises a processing system and a display, the processing system being configured to process the received pressure sensor data and to display the processed data on the display for a user as the pressure sensor data is being received from the apparatus.

31. The system of claim 29, wherein the pressure sensor configuration comprises a sample rate for sampling a tactile pressure and a transmit rate for transmitting the pressure sensor data corresponding to the sampled tactile pressure.

32. A system for obtaining and providing pressure feedback information, comprising:
an apparatus comprising a plurality of embedded tactile pressure sensors and a transceiver for transmitting pressure sensor data from the tactile pressure sensors;
a user equipment comprising a transceiver for receiving the pressure sensor data from the apparatus and for transmitting the pressure sensor data; and
a server for receiving the pressure sensor data from the user equipment;
wherein the server is configured to process the pressure sensor data with previous pressure sensor data in order to obtain trend information and is configured to provide the trend information to a user.

33. A system for obtaining and providing pressure feedback information, comprising:
an apparatus comprising a plurality of embedded tactile pressure sensors and a transceiver for transmitting pressure sensor data from the tactile pressure sensors;
a user equipment comprising a transceiver for receiving the pressure sensor data from the apparatus and for transmitting the pressure sensor data; and
a server for receiving the pressure sensor data from the user equipment;
wherein the apparatus is a helmet and the tactile pressure sensors are layered on an inner surface of the helmet to detect an impact force on the inner surface.

34. A system for obtaining and providing pressure feedback information, comprising:
an apparatus comprising a plurality of embedded tactile pressure sensors and a transceiver for transmitting pressure sensor data from the tactile pressure sensors;
a user equipment comprising a transceiver for receiving the pressure sensor data from the apparatus and for transmitting the pressure sensor data; and
a server for receiving the pressure sensor data from the user equipment;
wherein the apparatus is a steering wheel and the tactile pressure sensors are positioned on the steering wheel to detect whether one hand or two hands make full contact with the steering wheel.

35. A system for obtaining and providing pressure feedback information, comprising:
an apparatus comprising a plurality of embedded tactile pressure sensors and a transceiver for transmitting pressure sensor data from the tactile pressure sensors;
a user equipment comprising a transceiver for receiving the pressure sensor data from the apparatus and for transmitting the pressure sensor data; and
a server for receiving the pressure sensor data from the user equipment;
wherein the apparatus is a walking cane and the tactile pressure sensors are positioned on a bottom surface of the walking cane to detect walking and leaning patterns of a user using the walking cane.

36. A system for obtaining and providing pressure feedback information, comprising:
an apparatus comprising a plurality of embedded tactile pressure sensors and a transceiver for transmitting pressure sensor data from the tactile pressure sensors;
a user equipment comprising a transceiver for receiving the pressure sensor data from the apparatus and for transmitting the pressure sensor data; and
a server for receiving the pressure sensor data from the user equipment;
wherein the apparatus is a boxing glove and the tactile pressure sensors are positioned on an impact surface of the boxing glove to detect an impact force on the impact surface.

37. A system for obtaining and providing pressure feedback information, comprising:
an apparatus comprising a plurality of embedded tactile pressure sensors and a transceiver for transmitting pressure sensor data from the tactile pressure sensors;
a user equipment comprising a transceiver for receiving the pressure sensor data from the apparatus and for transmitting the pressure sensor data; and
a server for receiving the pressure sensor data from the user equipment;
wherein the apparatus is a sole and the tactile pressure sensors are positioned on the sole to detect cadence and leaning patterns of a user.

38. A system for obtaining and providing pressure feedback information, comprising:

an apparatus comprising a plurality of embedded tactile pressure sensors and a transceiver for transmitting pressure sensor data from the tactile pressure sensors;

a user equipment comprising a transceiver for receiving the pressure sensor data from the apparatus and for transmitting the pressure sensor data; and a server for receiving the pressure sensor data from the user equipment;

wherein the apparatus is a squeeze ball and the tactile pressure sensors are layered on a surface of the squeeze ball to detect a squeeze strength of a user.

39. A system for obtaining and providing pressure feedback information, comprising:

an apparatus comprising a plurality of embedded tactile pressure sensors and a transceiver for transmitting pressure sensor data from the tactile pressure sensors;

a user equipment comprising a transceiver for receiving the pressure sensor data from the apparatus and for transmitting the pressure sensor data; and a server for receiving the pressure sensor data from the user equipment;

wherein the apparatus is configured to transmit and the user equipment is configured to receive the pressure sensor data using low power radio.

40. The system of claim 39, wherein the low power radio is one selected from the group consisting of Bluetooth, Bluetooth low energy, ZigBee, and ANT.

41. A system for obtaining and providing pressure feedback information, comprising:

an apparatus comprising a plurality of embedded tactile pressure sensors and a transceiver for transmitting pressure sensor data from the tactile pressure sensors;

a user equipment comprising a transceiver for receiving the pressure sensor data from the apparatus and for transmitting the pressure sensor data; and a server for receiving the pressure sensor data from the user equipment;

wherein the apparatus is configured to transmit and the user equipment is configured to receive the pressure sensor data with an associated time stamp.

42. A system for obtaining and providing pressure feedback information, comprising:

an apparatus comprising a plurality of embedded tactile pressure sensors and a transceiver for transmitting pressure sensor data from the tactile pressure sensors;

a user equipment comprising a transceiver for receiving the pressure sensor data from the apparatus and for transmitting the pressure sensor data; and a server for receiving the pressure sensor data from the user equipment;

wherein the user equipment is configured to receive a GPS signal, to determine GPS locations based on the GPS signal, to associate the GPS locations with the received pressure sensor data, and to transmit the GPS locations with the associated pressure sensor data to the server.

43. The system of claim 42, wherein the server is configured to correlate the GPS locations with the associated pressure sensor data to obtain velocity, acceleration, and elevation information as related to the associated pressure sensor data.

44. A system for obtaining and providing pressure feedback information, comprising:

an apparatus comprising a plurality of embedded tactile pressure sensors and a transceiver for transmitting pressure sensor data from the tactile pressure sensors;

a user equipment comprising a transceiver for receiving the pressure sensor data from the apparatus and for transmitting the pressure sensor data; and a server for receiving the pressure sensor data from the user equipment;

wherein the server is configured to send a request to the user equipment with information on when the pressure sensor data should be collected by the apparatus, a frequency of upload by the apparatus, whether the user equipment should obtain GPS coordinates in association with the received pressure sensor data, and a frequency that the user equipment should obtain the GPS coordinates.

45. An apparatus for wireless communication, comprising:

a body;

a plurality of tactile pressure sensors embedded within the body on at least two opposing surfaces;

a transceiver; and a processing system coupled to the transceiver and to the tactile pressure sensors and configured to receive tactile pressure information from the tactile pressure sensors and to contact emergency services through the transceiver when the tactile pressure information indicates simultaneous activation of the tactile pressure sensors on the at least two opposing surfaces consistent with a squeezing of the body.

46. An apparatus for wireless communication, comprising:

a processing system;

a transceiver coupled to the processing system; and a display coupled to the processing system, wherein the processing system is configured to:

transmit a pressure sensor configuration comprising a sample rate for sampling a tactile pressure and a transmit rate for transmitting the pressure sensor data corresponding to the sampled tactile pressure;

receive pressure sensor data at the transmit rate and sampled at the sample rate, the pressure sensor data comprising a plurality of sampled tactile pressures and time stamps associated with the sampled tactile pressures;

process the received pressure sensor data; and display the processed data on the display.

47. The apparatus of claim 46, wherein the processing system is further configured to receive a GPS signal, to determine a GPS location based on the GPS signal, to associate the GPS location with the received pressure sensor data, and to transmit the GPS location with the associated pressure sensor data to a server.

48. The apparatus of claim 46, wherein the processing system is configured to receive the pressure sensor data through low power radio.

49. The apparatus of claim 48, wherein the low power radio is one selected from the group consisting of Bluetooth, Bluetooth low energy, ZigBee, and ANT.

50. An apparatus for wireless communication, comprising:

a surface on which a pressure can be exerted;

a plurality of pressure sensors embedded in the surface;

a controller coupled to the pressure sensors; and a transceiver coupled to the controller, wherein the controller is configured to:

receive a pressure sensor configuration comprising a sample rate for sampling a tactile pressure and a transmit rate for transmitting the pressure sensor data corresponding to the sampled tactile pressure;

obtain pressure sensor data from the pressure sensors; and transmit the pressure sensor data and an associated time stamp to a user equipment.

51. The apparatus of claim 50, wherein the apparatus is one selected from the group consisting of a sole, a shoe, a boot, a helmet, a boxing glove, a cane, a squeeze ball, and a steering wheel.

52. The apparatus of claim 50, wherein the controller is configured to transmit using low power radio.

53. The apparatus of claim 52, wherein the low power radio is one selected from the group consisting of Bluetooth, Bluetooth low energy, ZigBee, and ANT.

54. A method of wireless communication, comprising:
receiving configuration information at a tactile pressure sensor from a user equipment; and
transmitting pressure sensor data to the user equipment based on the configuration information, wherein the configuration information comprises a sample rate for sampling a tactile pressure and a transmit rate for transmitting the pressure sensor data corresponding to the sampled tactile pressure.

55. The method of claim 54, wherein the tactile pressure sensor data comprises a plurality of sampled tactile pressures sampled at the sample rate and time stamp information associated with the sampled tactile pressures.

56. An apparatus for wireless communication, comprising:
means for receiving configuration information at a tactile pressure sensor from a user equipment; and
means for transmitting pressure sensor data to the user equipment based on the configuration information, wherein the configuration information comprises a sample rate for sampling a tactile pressure and a transmit rate for transmitting the pressure sensor data corresponding to the sampled tactile pressure.

57. The apparatus of claim 56, wherein the tactile pressure sensor data comprises a plurality of sampled tactile pressures sampled at the sample rate and time stamp information associated with the sampled tactile pressures.

58. A computer program product, comprising:
a non-transitory computer-readable medium comprising code for:
receiving configuration information at a tactile pressure sensor from a user equipment; and
transmitting pressure sensor data to the user equipment based on the configuration information, wherein the configuration information comprises a sample rate for sampling a tactile pressure and a transmit rate for transmitting the pressure sensor data corresponding to the sampled tactile pressure.

59. The computer program product of claim 58, wherein the tactile pressure sensor data comprises a plurality of sampled tactile pressures sampled at the sample rate and time stamp information associated with the sampled tactile pressures.

60. An apparatus for wireless communication, comprising:
a processing system configured to:
receive configuration information at a tactile pressure sensor from a user equipment; and
transmit pressure sensor data to the user equipment based on the configuration information, wherein the configuration information comprises a sample rate for sampling a tactile pressure and a transmit rate for transmitting the pressure sensor data corresponding to the sampled tactile pressure.

61. The apparatus of claim 60, wherein the tactile pressure sensor data comprises a plurality of sampled tactile pressures sampled at the sample rate and time stamp information associated with the sampled tactile pressures.

* * * * *